United States Patent [19]

Kohayakawa

[11] Patent Number: 5,777,718
[45] Date of Patent: Jul. 7, 1998

[54] EYE REFRACTOMETER

[75] Inventor: Yoshimi Kohayakawa, Yokohama, Japan

[73] Assignee: Canon Kabushiki Kaisha, Tokyo, Japan

[21] Appl. No.: 803,104

[22] Filed: Feb. 20, 1997

Related U.S. Application Data

[63] Continuation of Ser. No. 174,024, Dec. 28, 1993, abandoned.

[30] Foreign Application Priority Data

| Dec. 31, 1992 | [JP] | Japan | 4-361043 |
| Jan. 25, 1993 | [JP] | Japan | 5-029873 |
| Sep. 21, 1993 | [JP] | Japan | 5-259208 |

[51] Int. Cl.$^6$ ........................... A61B 3/10
[52] U.S. Cl. ........................... 351/211; 351/205
[58] Field of Search ........................... 351/205, 204, 351/200, 208, 211, 221, 245, 212, 237

[56] References Cited

U.S. PATENT DOCUMENTS

| 3,664,631 | 5/1972 | Guiton | 351/211 |
| 4,609,287 | 9/1986 | Kohayakawa | 356/124 |
| 4,697,895 | 10/1987 | Sekiguchi et al. | 351/243 |
| 4,704,012 | 11/1987 | Kohayakawa et al. | 359/493 |
| 4,820,037 | 4/1989 | Kohayakawa et al. | 351/211 |
| 5,144,346 | 9/1992 | Nakamura et al. | 351/208 |
| 5,231,430 | 7/1993 | Kohayakawa | 351/243 |
| 5,237,351 | 8/1993 | Kohayakawa et al. | 351/243 |
| 5,249,003 | 9/1993 | Kohayakawa | 351/211 |
| 5,371,558 | 12/1994 | Kohayakawa | 351/211 |

*Primary Examiner*—Huy Mai
*Attorney, Agent, or Firm*—Fitzpatrick, Cella, Harper & Scinto

[57] ABSTRACT

An eye refractometer has two to three visual target systems provided for right and left eyes. Each of the visual target systems has a visual target and diopter varying device for making the visual target variable in diopter relative to an eye to be examined. An optical path coupler is provided between the eye to be examined and the diopter varying device with respect to at least one of the visual target systems. An eye refractive power measuring device is also provided for projecting light from outside of the visual target systems through the optical path coupling device and receiving the light from the eye to be examined to thereby measure the refractive power of the eye to be examined. Also included is a switchover device for switching the eye refractive power measuring device from measuring the refractive power of one eye to measuring the refractive power of the other eye by moving the refractive power measuring device left or right.

14 Claims, 15 Drawing Sheets

5,777,718

EYE REFRACTOMETER

This application is a continuation of application Ser. No. 08/174,024 filed Dec. 28, 1993, now abandoned.

BACKGROUND OF THE INVENTION

1. Field of the Invention

This invention relates to eye refractometers widely used in ophthalmic hospitals or the like.

2. Related Background Art

In conventional eye refractometers, so-called single eye viewing is popular in which, during the measurement of the refraction of an eye to be examined, measurement is effected with a fixation visual target presented only to an eye to be measured.

In the above-described prior art, however, the fixation visual target is not presented to the other eye and therefore, the effect of the adjustment of the other eye intervenes in the adjustment of the eye to be examined to thereby bring about a state called instrument myopia which may give birth to an error in the measured value of the refraction of the eye to be examined.

SUMMARY OF THE INVENTION

It is an object of the present invention to eliminate the above-noted disadvantage and to provide an eye refractometer which can eliminate the effect of the other eye on the adjustment of an eye to be examined and reliably guide the eye to be examined to a far point.

Other objects of the present invention will become apparent from the following detailed description of some embodiments of the invention.

DESCRIPTION OF THE PREFERRED EMBODIMENTS

Figure 1:
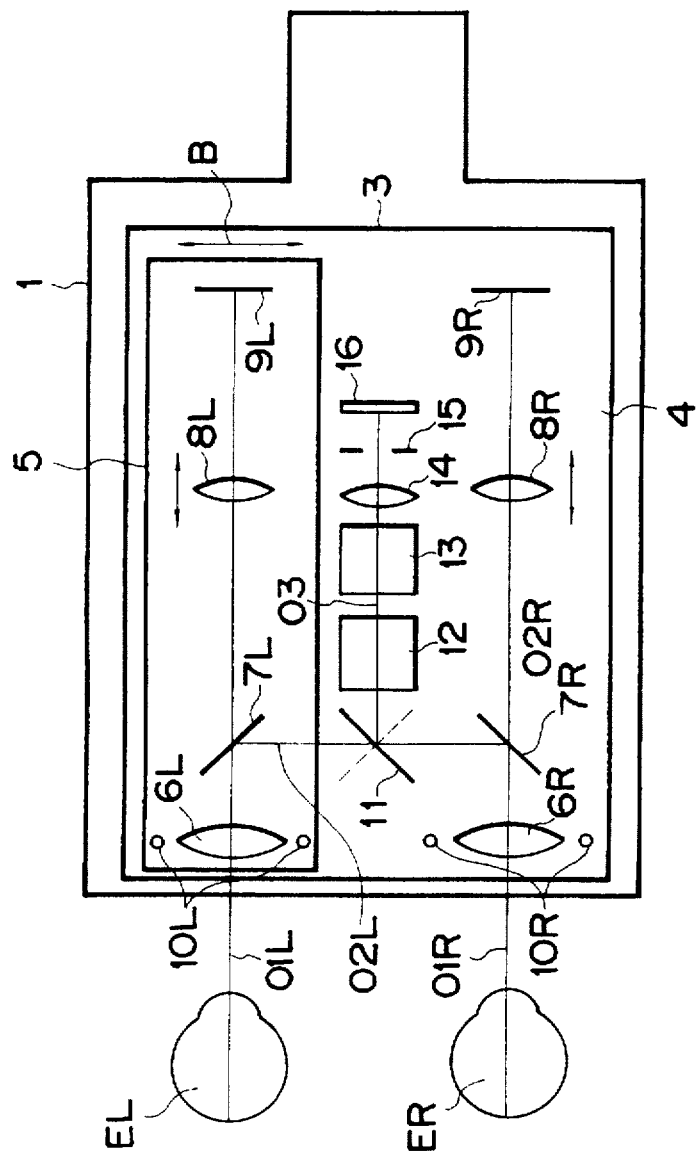
FIG. 1 is a plan view of a first embodiment of the present invention.

The present invention will hereinafter be described in detail with respect to some embodiments thereof shown in the drawings.

Figure 2:
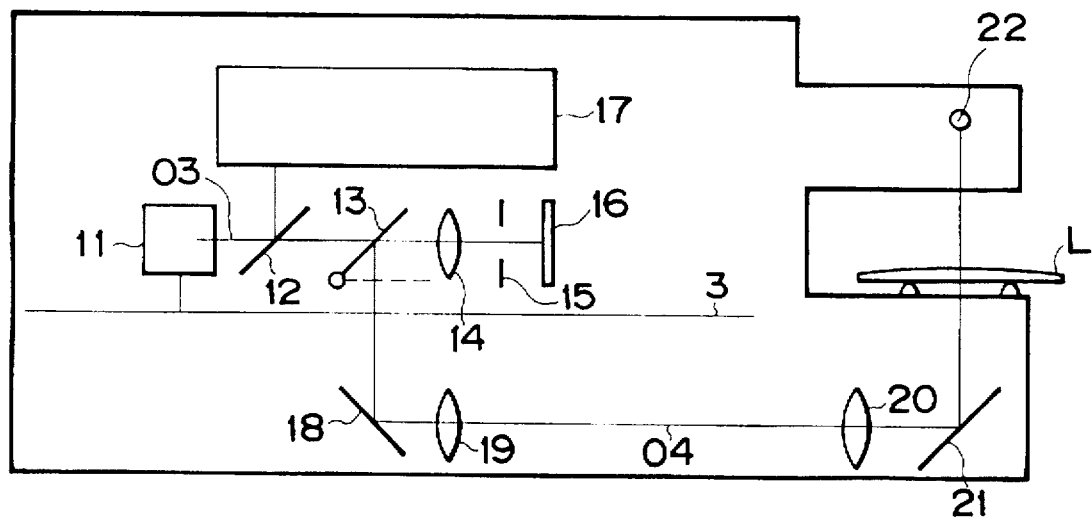
FIG. 2 is a side view of the first embodiment.
Figure 3:
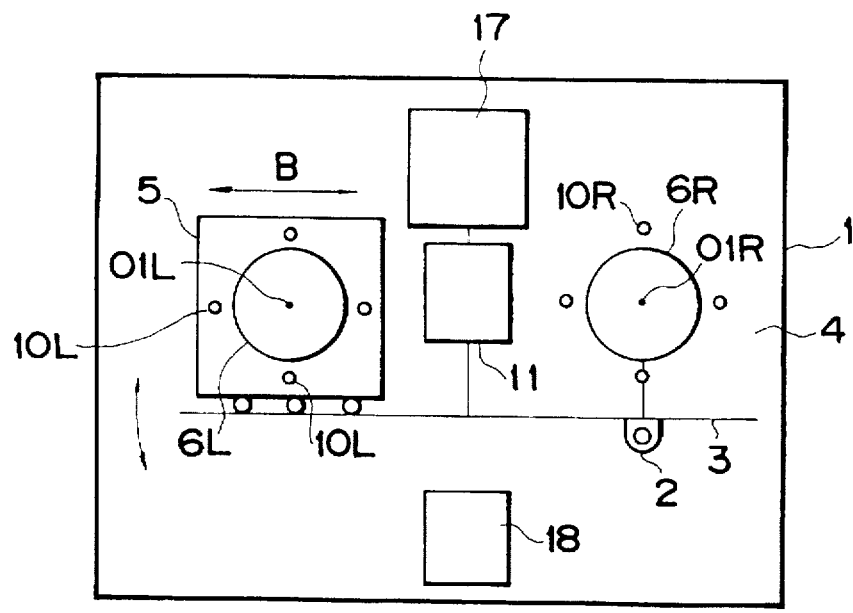
FIG. 3 is a front view of the first invention.

FIG. 1 is a plan view of an eye refractometer according to a first embodiment, FIG. 2 is a side view thereof, and FIG. 3 is a front view thereof. The first embodiment is an apparatus having the functions of a refractometer, a keratometer and a lens meter compounded, and as shown in FIG. 3, an eye measuring optical stand 3 rotatable about a center axis of rotation 2 is provided on a measuring head 1 placed on a sliding stand, not shown. A right eye visual target system 4 is disposed at the right on the upper portion of the eye measuring optical stand 3, and a left eye visual target system 5 movable in the direction of the pupil distance B is disposed at the left. Lenses 6R, 6L dichroic mirrors 7R, 7L, movable lenses 8R, 8L movable in the direction of the optical axis and visual targets 9R, 9L are disposed symmetrically on the optical axes 01R and 01L, respectively, ahead of eyes ER and EL to be examined, and cornea curvature measuring light sources 10R and 10L are provided at four locations above and below and at the right and left of the lenses 6R and 6L.

Optical paths 02R and 02L which are the directions of reflection of the dichroic mirrors 7R and 7L intersect each other on a pivotable switchover mirror 11, and on an optical path 03 reflected by the switchover mirror 11, there are disposed in succession a dichroic mirror 12 for upwardly during the optical path, a movable mirror 13 for changing over a beam of light from an optical path 04 for the lens meter and a beam of light from the direction of the optical path 03, a lens 14, a stop 15 having an opening at the center thereof and an area image sensor 16, the output of which is connected to control means such as a computer, not shown. Also, in the direction of reflection of the dichroic mirror 12, there is provided refraction measuring means 17 comprised of an infrared light source, a photoelectric sensor and an infrared TV camera, not shown.

The optical path 04 below the movable mirror 13 is an optical path for the lens meter provided on the measuring head 1, and on this optical path, there are disposed, in succession from the movable mirror 13 side, a mirror 18, a lens 19, a lens 20, a mirror 21, a lens L to be examined such as of spectacles, and a light source 22. The mirror 18, the lens 19, the lens 20, the mirror 21 and the light source 22 are provided on the measuring head 1 independently of the eye measuring optical stand 3.

Alignment is effected prior to measurement. An examinee sits down in front of the apparatus, and the sliding stand is slid so that the center of the pupil of the right eye ER and the optical axis 01R coincide with each other as seen by an infrared TV camera provided in the refraction measuring means 17. The switchover mirror 11 is then switched over with the eye measuring optical stand 3 kept horizontal relative to the measuring head 1, and the left eye fixation visual target system 5 is slid in the eye width direction 13 to adjust the eye width while the left eye is observed by means of the infrared TV camera.

Generally, the height of the right and left eyes differ from each other. For the optometropic examine, this state is equivalent to a state in which vertical prisms are put in, and are in a diploic state, and it is impossible to see the visual target with two eyes. Therefore, the eye measuring optical stand 3 is rotated about the center axis of rotation 2 to thereby adjust the optical axes 01R and 01L so as to coincide with the center of the pupils of the left and right eyes EL and ER. Assuming that the instrument is properly positioned and the pupils of the eyes EL and ER coincide with the front focal position of the lenses 6R and 6L, the beam passing the pupils becomes parallel in the optical path to the lenses 6R and 6L and therefore, the image displayed on an anterior eye part observation TV set by the sliding of the left eye visual target system 5 will not vary from its in-focus state and magnification. Further, the focus will not change in the measurement by the keratometer.

The measurement of the right eye ER is first effected in the measurement of eye refraction. That is, the movable lenses 8R, 8L and the visual targets 9R, 9L are set to a state in which they appear to be at infinity, and the measurement of eye refraction is effected. A beam of infrared light emitted from a light source, not shown, in the refraction measuring means 17 is reflected by the dichroic mirror 12, the switchover mirror 11 and the dichroic mirror 7R and passes through the lens 6R to the right eye ER to be examined. The reflected light from the fundus of the eye returns along the same course and is received by a photoelectric sensor, not shown, provided in the refraction measuring means 17, and the refraction power of the eye is calculated from the state of the received beam of light. The principle of this eye refraction measurement is well known and is not described in detail herein.

Figure 29:
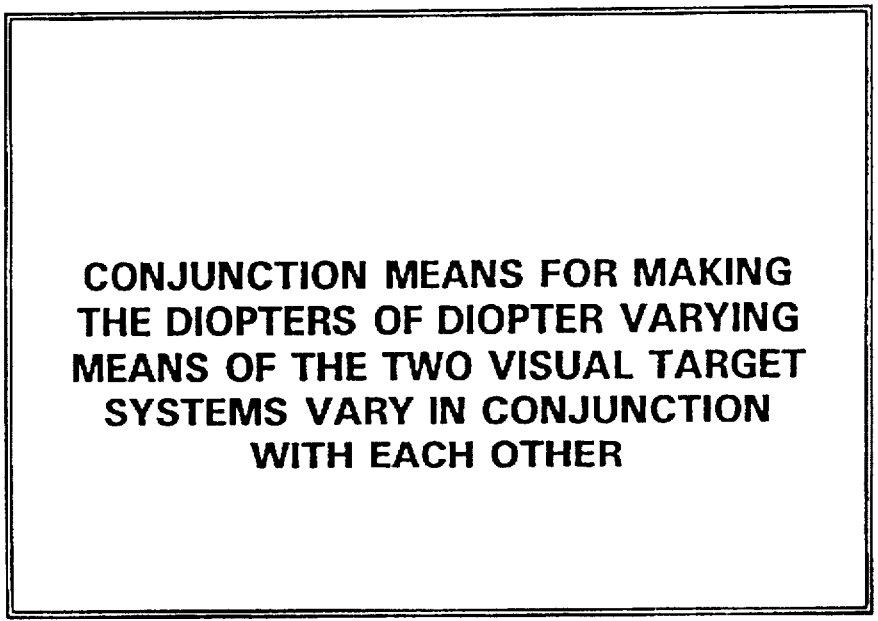
FIG. 29 shows a block diagram of the conjunction means.

In this state, the substantially correct eye refractive power is calculated but there is the possibility of relaxation of the eye so that the accomodation by the eye is not sufficient and therefore, measurement is further effected with fogging applied to the eye. The left and right eyes EL and ER often have the same degree of diopter and the accomodation change effected by the fogging can generally be considered of the same degree for the left and right eyes and therefore, the movable lenses 8R and 8L are moved in conjunction with each other keeping the diopter of the target 9L hyperopic by 1 to 1.5D from the diopter of the target 9R, thereby rendering the measuring head a means for making the diopters of the lenses 8R and 8L vary in conjunction with each other, as seen in FIG. 29.

Fogging measurement is effected several times and when the measured value has become stable, the measurement of the left eye EL is effected. The switchover mirror 11 is switched over to bring the left eye EL into a measurable state, and the movable lens 8R is adjusted so that the right eye ER side may assume a diopter fogging toward the hyperopia by about 1–1.5D relative to the measured right eye refraction value. The visual target of the right eye ER is fixed in this state, and the fogging state of the left eye EL is changed several times and guided to a relaxation state of accomodation, and refraction measurement is effected. When the measurement is to be started from the left eye EL, the above mentioned process is reversed. Also, for an examinee to whom diplopia occurs inevitably in biocular viewing, measurement will be effected with the other eye visual target turned off.

During the measurement of cornea curvature by the keratometer, the four light sources 10R on the right eye ER side which is the eye to be measured are first turned on. The corneal reflected light arrives at the switchover mirror 11 via the lens 6R and the dichroic mirror 7R. The beam of light is reflected by the switchover mirror 11, is transmitted through the dichroic mirror 12 and forms a corneal reflection image on the area image sensor 16 via the lens 14 and the stop 15. It is to be understood that at this time, the movable mirror 13 is retracted out of the optical path as indicated by dotted line in FIG. 2. The corneal reflection image formed on the area image sensor 16 is image-processed by a computer, whereby the radius of curvature of the cornea is found. The cornea curvature of the left eye EL is likewise calculated with the switchover mirror 11 changed over. The principle of this cornea curvature measurement is also well known and is not described in detail herein.

During the use of the lens meter, the examiner places the lens L to be examined at a predetermined position and depresses a measurement switch. The light source 22 is turned on, and the beam of light transmitted through the lens L to be examined passes along the optical path 04 and is reflected by the movable mirror 13 to be moved upwardly, and is imaged on the area image sensor 16 via the lens 14 and the stop 15. The light source image on the area image sensor 16 is analyzed by a computer, not shown, and the degree of correction performed by the lens L to be examined is calculated. The principle of this lens degree calculation is also well known and is not described in detail herein.

Also, when the examinee wears a pair of spectacles, the degree of correction performed by the spectacles is first measured, and during the measurement of eye refraction, fogging far by about 1–1.5D from the measured degree of the spectacles can be given, and then the measurement of eye refraction can be effected to thereby ensure the elimination of the accommodation of the eye to be examined. The setting of these visual target diopters may preferably be automatically effected by a computer, not shown.

The drive system for the eye measuring optical stand 3 may be of the electrically operated type or the manually operated type. Also, an adjustment such as tilting the eye measuring optical stand 3 is made in order to bring the optical axes 01R and 01L into coincidence with the visual axis, and by this tilting operation, an error is created in the axial angle measured by the cornea curvature measurement and the lens meter measurement, but this error is slight and may be neglected, or a mechanism for measuring the angle of inclination of the eye measuring optical stand 3 may be provided so that the error may be corrected by a computer.

Also, during the measurement by the lens meter, it is unnecessary for the eye measuring optical stand 3 to be inclined and therefore, the eye measuring optical stand 3 can be returned to its horizontal position, and then the measurement can be effected.

Further, during the measurement of the cornea curvature, the eye measuring optical stand 3 is inclined to thereby shift the optical path, and the effect in the stop 15 may sometimes be somewhat affected by the eye width value, but this does not pose a great problem. The stop 15 may be designed to be inserted as an actual stop having an opening during the measurement of the cornea curvature, or may be constructed of a dichroic mirror or the like for selectively annularly intercepting the wavelength of the beam of light used for the measurement of the cornea curvature.

Figure 4:
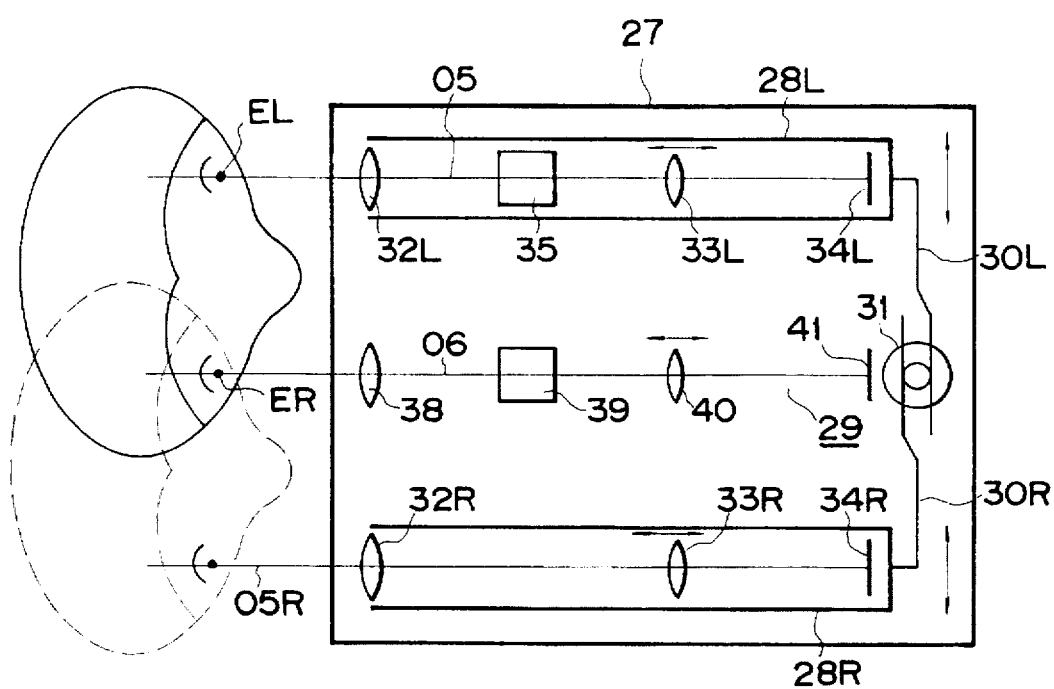
FIG. 4 is a plan view of a second embodiment of the present invention.
Figure 5:
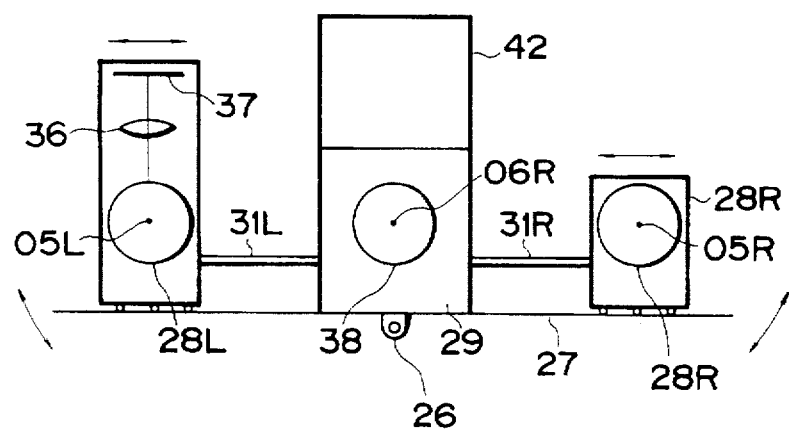
FIG. 5 is a front view of the second embodiment.

FIG. 4 is a plan view of a second embodiment of the present invention, and FIG. 5 is a front view thereof. As in the first embodiment, optical paths O5R, O6 and O5L are provided parallel to one another from right to left on the upper portion of a table 27 mounted on a base provided with a sliding mechanism capable of three-dimensional alignment and vertically tiltable about a center axis of rotation 26. A right eye visual target system 28R movable relative to the table 27, objective refraction measuring means 29 fixed to the table 27, and a left eye visual target system 28L movable relative to the table 27 are provided on the optical paths O5R, O6 and O5L, respectively, and interlocking mechanisms 30R and 30L are connected to the right eye visual target system 28R and the left eye visual target system 28L, respectively, so that the right and left eye visual target systems may be moved by a desired distance in the direction of the eye width by the rotation of a step motor 31 connected to the interlocking mechanisms 30R and 30L. Also, the right eye visual target system 28R and the left eye visual target system 28L are designed to be located always equidistantly from the objective refraction measuring means 29.

A lens 32R, a lens 33R movable in the direction of the optical axis and a visual target 34R are provided in succession from the eye in the right eye visual target system 28R, and a lens 32L, a dichroic mirror 35 for upwardly dividing the optical path O5L, a lens 33L movable in the direction of the optical axis and a visual target 34R are provided in succession from the eye in the left eye visual target system 28L. As shown in FIG. 5, a lens 36 and a two-dimensional CCD 37 are provided in the direction of reflection of the dichroic mirror 35, and are utilized during the alignment of the eye width and inclination. A lens 38, a dichroic mirror 39, a movable lens 40 movable in the direction of the optical axis and a visual target 41 are disposed in succession forwardly of the optical path O6, and the objective refraction measuring means 29 and a containing unit 42 for a TV camera for anterior eye part observation shown in FIG. 5 are disposed above the dichroic mirror 39.

The examinee first sits down with the right eye ER positioned forwardly of the optical path O6 and the left eye EL positioned forwardly of the optical path O5L in order to have the refraction of the right eye ER measured. The examiner moves the table 27 three-dimensionally by the use of a sliding mechanism, not shown, and effects alignment so that the optical path O6 may be exactly positioned forwardly of the right eye ER.

Figure 6:
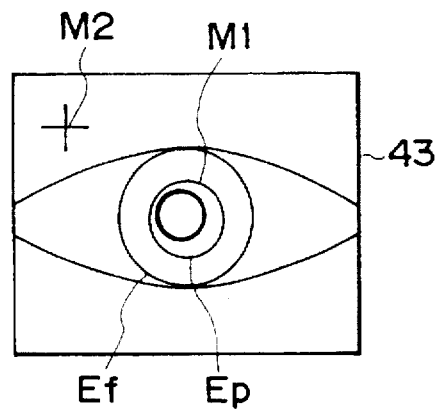
FIG. 6 is an illustration of the image of an anterior eye part on a TV monitor.

FIG. 6 is an illustration of an image on a TV monitor 43 which has been picked up by the anterior eye part observation TV camera provided in the containing unit 42. The image of the anterior eye part and a visual target M1 coincident with the position of the optical path O6 are displayed on the TV monitor 43, and alignment is effected so that the pupil Ep of the right eye ER may coincide with the visual target M1. The image of the left eye EL is displayed on the two-dimensional CCD 37 provided in the left eye visual target system 28L. This image of the left eye is analyzed by a computer and the position of the pupil of the left eye EL is detected. The detected position of the pupil is displayed as a visual target M2 on the TV monitor 43. The examiner adjusts the distance between the visual target systems and the inclination of the stand 27 so that the visual target M2 too coincides with the visual target M2.

When the alignment is completed, the examiner effects the measurement of the right eye ER as in the first embodiment. When the measurement of the right eye ER is completed, the examiner slides the table 27 laterally so that the left eye EL is positioned forwardly of the optical path O6 and the right eye ER may be positioned on the optical path O5R, and effects the measurement of the left eye EL. The design of the embodiment is made such that the right eye visual target system 28R and the left eye visual target system 28L are moved in conjunction in the direction of the pupil distance by the interlocking mechanisms 30R and 30L so the distances between visual target systems 28L, 28R and the optical path O6 are kept equal, and therefore, when for the measurement of the left eye, the table 27 is slid laterally and alignment is effected so that the pupil Ep of the left eye EL and the visual target M1 coincide with each other, it is possible to effect measurement without adjusting the right eye visual target system 28R. The operation can therefore be simplified. The design of the embodiment may also be made such that the alignment operation including the pupil distance adjusting operation, the operation of tilting the table 27, etc. is automatically performed by a computer control using the image on the TV monitor 43.

Figure 7:
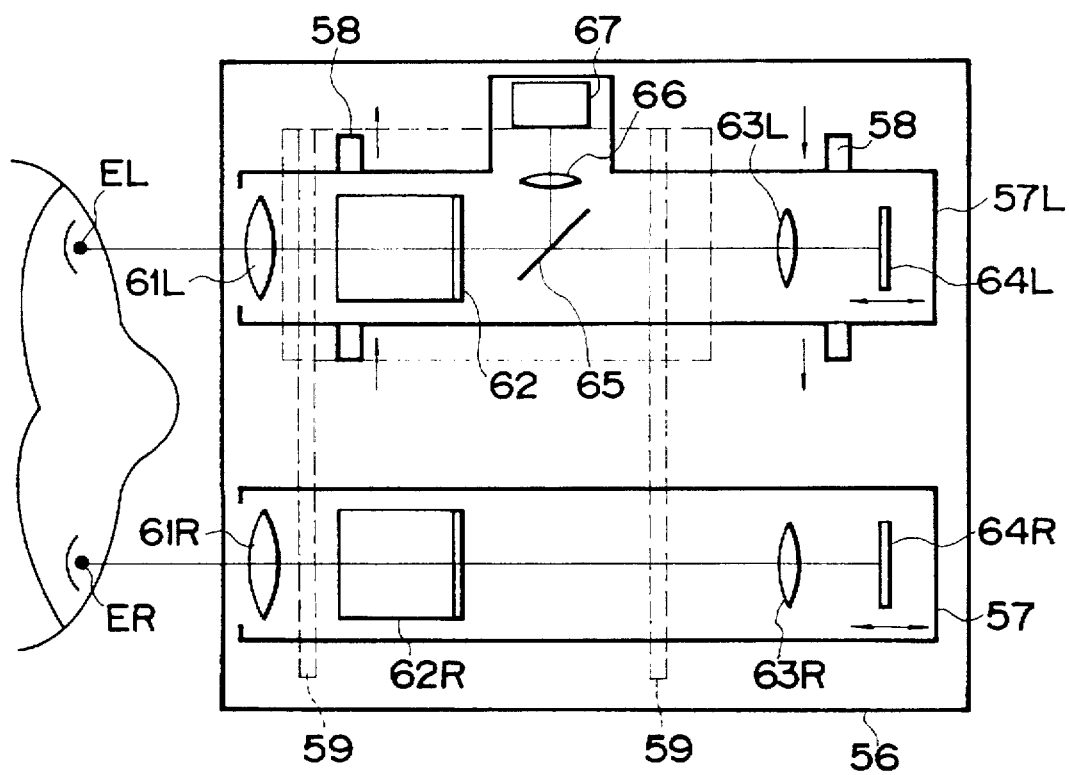
FIG. 7 is a plan view of a third embodiment of the present invention.
Figure 8:
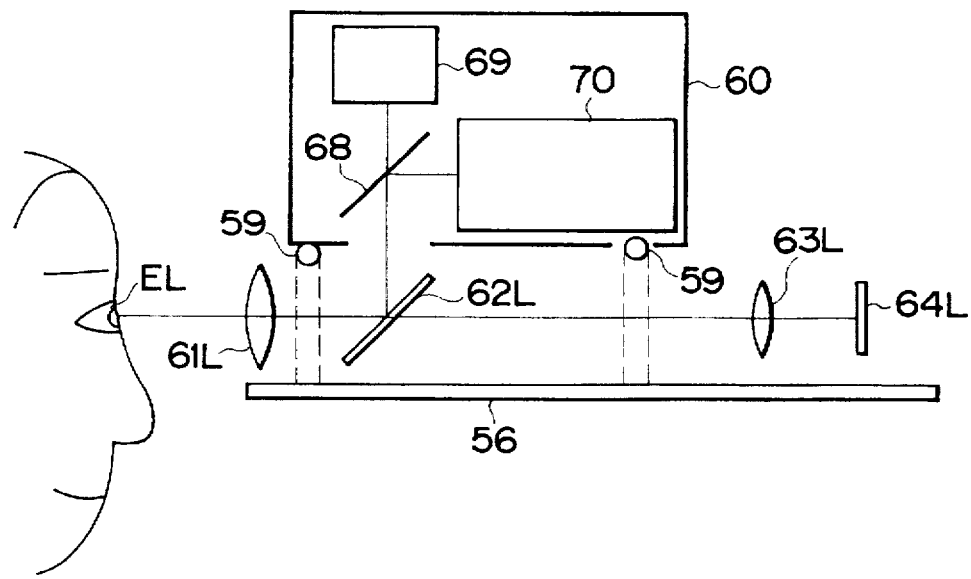
FIG. 8 is a side view of the third embodiment.
Figure 9:
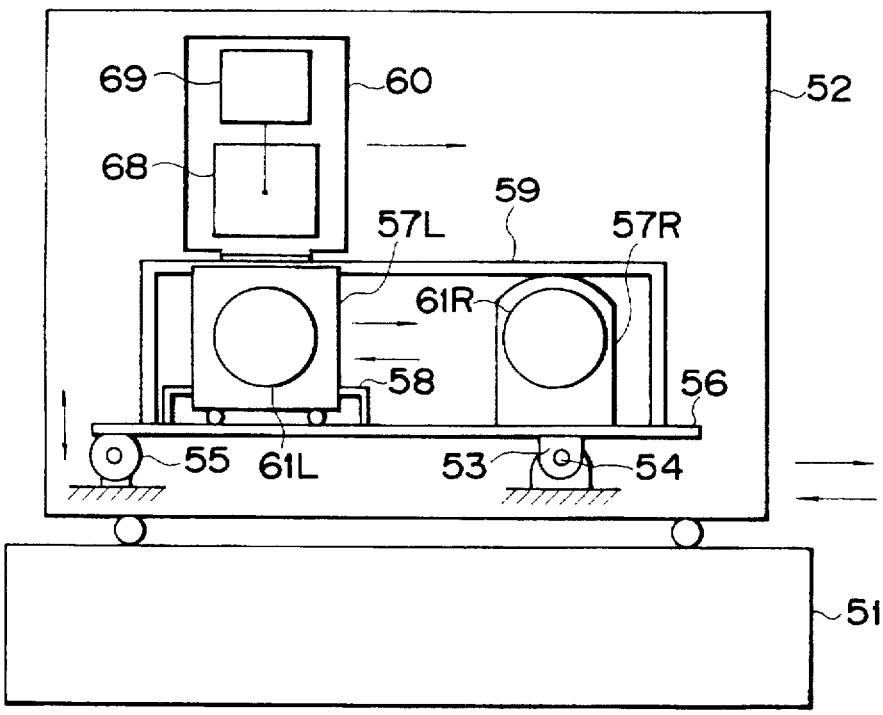
FIG. 9 is a front view of the third embodiment.

FIG. 7 is a plan view of a third embodiment of the present invention, FIG. 8 is a side view thereof, and FIG. 9 is a front view thereof. As shown in FIG. 9, a measurement head 52 having a roller or the like mounted on the lower portion thereof and slidable horizontally is placed on a base 51 provided with bead fixing means such as a chin rest, not shown. Within the measurement head 52, various measuring units are placed on the upper surface thereof and a table 56 vertically tiltable about a shaft 54 extending through a bearing 53 by a motor 55 provided on the other end is provided on the underside thereof. On the upper portion of the table 56, a right eye visual target system 57R fixed to the stand 56 and a left eye visual target system 57L mounted so as to be manually or electrically slidable in the direction of the pupil distance along two guides 58 provided at the front and rear are provided parallel to each other. Above the visual target systems 57R and 57L, two guides 59 of the examinee are mounted on the table 56 and crossing over the two visual target systems 57R and 57L are installed parallel to each other.

Refraction measuring means 60 electrically or manually movable above the visual target systems 57R and 57L is placed on the guides 59, which support the refraction measuring means 60 and provide a guide when the refraction measuring means 60 slides laterally.

In the right eye visual target system 57R, an objective lens 61R, a dichroic mirror 62R for upwardly dividing the optical path, a lens 63R and a visual target 64R movable in the direction of the optical path and having its position controllable by a computer are provided in succession from the right eye ER side.

Also, in the left eye visual target system 57L, an objective lens 61L, a dichroic mirror 62L for upwardly dividing the optical path, a dichroic mirror 65 for sideways dividing the optical path, a lens 63L and a visual target 64L movable in the direction of the optical path are provided in succession from the left eye EL side, and a lens 66 and image pickup means 67 for picking up the image of the anterior eye part of the left eye EL are provided in the direction of reflection of the dichroic mirror 65. Within the refraction measuring means 60, there are provided a dichroic mirror 68 on which beams of light from the dichroic mirrors 62R and 62L below it are incident, and a TV camera 69 for picking up the image of the anterior eye part, and a refraction measuring unit 70 comprising a light source, an image pickup system, etc. is disposed in the direction of reflection of the dichroic mirror 68.

Figure 10:
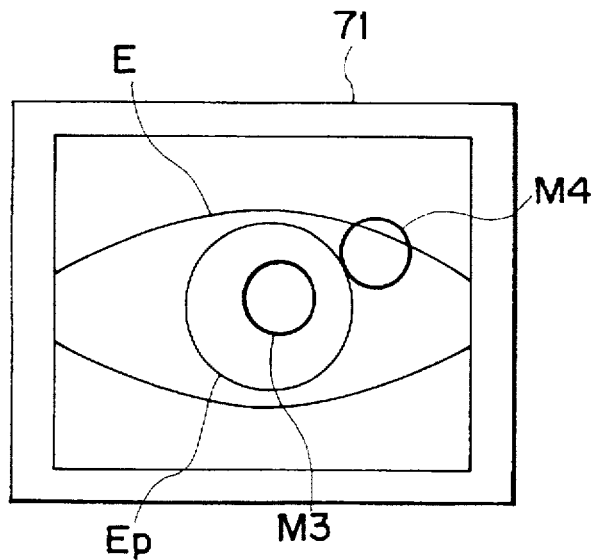
FIG. 10 is an illustration of the image of the left eye on a TV monitor.

During alignment, the refraction measuring means 60 is disposed on the right eye visual target system 57R, and the optical axis of the dichroic mirror 62R and the optical axis of the refraction measuring means 60 are brought into coincidence with each other. In this state, the examinee sits down in front of the apparatus and has his or her face fixed to a face rest, not shown. The examiner moves the measurement head 52 observing the image of the right eye picked up by the TV camera 69 and displayed on a TV monitor 71 shown in FIG. 10, and adjusts the apparatus so that the pupil Ep of the right eye and an annular alignment visual target M3 may become concentric circles.

Figure 11:
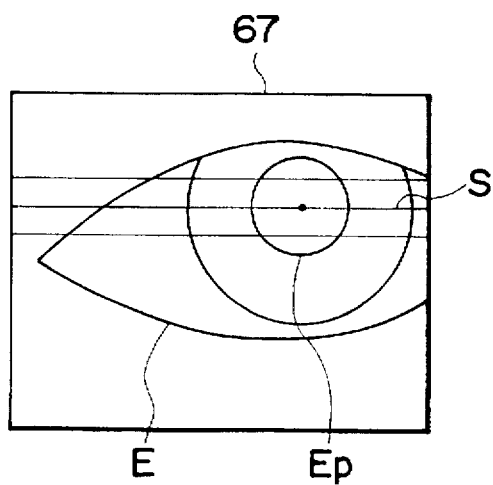
FIG. 11 is an illustration of the image of the left eye on image pickup means.

The alignment of the left eye EL is then effected. In the left eye visual target system 57L, the image of the left eye is picked up by the image pickup means 67, as shown in FIG. 11. The computer analyzes video signals of the scanning lines S on the image of the left eye and calculates the position of the left eye EL. The calculated position of the left eye is displayed on the TV monitor 71 as an alignment visual target M4 being eccentric by the amount of deviation from the alignment coincidence position. The examiner moves the left eye visual target system 57L in the direction of the eye width, and further drives the motor 55 and adjusts the inclination of the table 56, thereby aligning of the left eye EL.

When the alignment is completed, the measurement of the refraction of the right eye ER is effected by the use of the refraction measuring means 60, and then the refraction measuring means 60 is manually or electrically slid along the guides 59 and is moved so that the optical axis may coincide with above the left eye visual target system 57L, and the measurement of the refraction of the left eye EL is carried out. The design of the embodiment is made such that even when the left eye visual target system 57L is moved to the left or the right, the refraction measuring means 60 slides by the same amount and the optical axes of the left eye visual target system 57L and refraction measuring means 60 always coincide with each other.

When the alignment of the left eye EL is effected, the distance between the pupils can be secondarily calculated from the positions of the left eye visual target system 57L and alignment visual target M4 before the alignment work.

Figure 12:
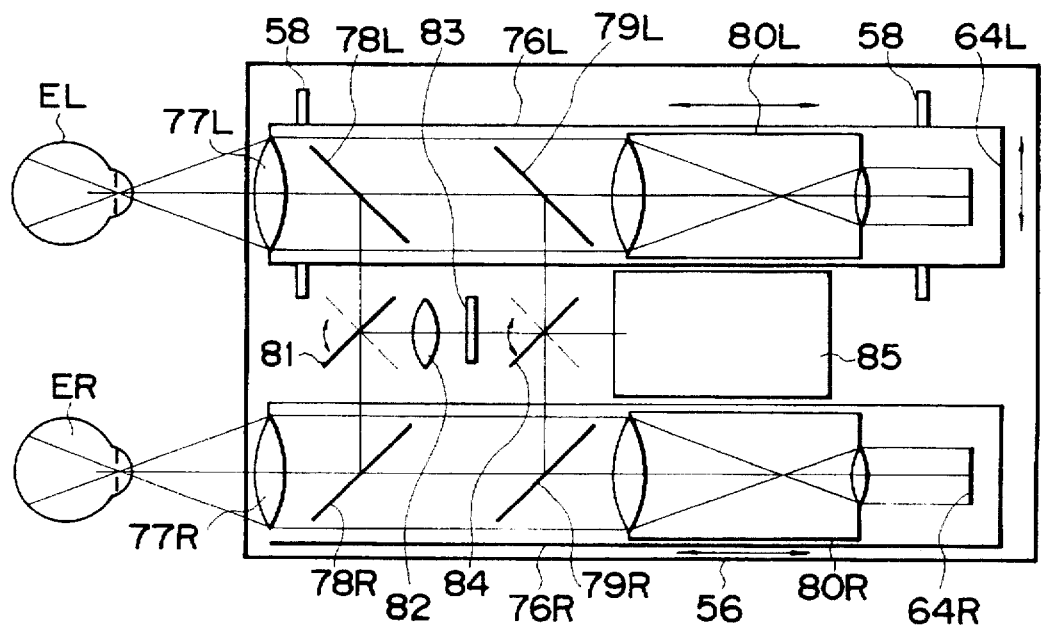
FIG. 12 is a plan view of a fourth embodiment of the present invention.

FIG. 12 is a plan view of a fourth embodiment of the present invention. The same members as those in the third embodiment are given the same reference characters and need not be described. In right and left visual target systems 76R and 76L placed on the table 56, objective lenses 77R, 77L, dichroic mirrors 78R, 78L, dichroic mirrors 79R, 79L, movable lens units 80R, 80L movable in the direction of the optical axis and comprised of a plurality of lenses, and visual targets 64R, 64L are provided in succession so as to be symmetrical and parallel to each other. A switchover mirror 81 for changing over the optical paths of the right and left eyes is provided on the reflection side of the dichroic mirrors 78R, 78L, and a lens 82 which comprises anterior eye part observation means and an image pickup element 83 are provided in succession in the direction of reflection of the switchover mirror 81. Also, a switchover mirror 84 for changing over the optical paths of the right and left eyes is provided on the reflection side of the dichroic mirrors 79R, 79L and further, refraction measuring means 85 for measuring the refraction of the eyes is provided on the reflection side of the switchover mirror 84.

During alignment, the switchover mirror 81 is changed over to bring about a state for measuring the right eye ER, and in this state, alignment is effected so that the eye ER to be examined, the image of which is outputted to an anterior eye part observation TV, may come to the center of the image pickup field. The switchover mirror 81 is then rotated by 90° to bring about a state for measuring the left eye, and the left eye visual target system 76L is moved in the direction of the eye width to adjust the distance between the pupils, and the table 56 is tilted and alignment is effected so that the eye EL to be examined may come to the center of the image pickup field. Subsequently, by providing means for measuring the position of the left eye visual target system 76L, the distance between the pupils can be measured. The switchover mirror 84 is changed over, whereby the right and left eyes are successively measured. At this time, the switchover mirror 81 and the switchover mirror 84 are synchronized with each other so that the state of the eye being measured may be observed. In this case, the order of the refraction measurement may be begun from any of the right and left eyes.

In the optical systems of the visual target systems 76R and 76L, the objective lenses 77R, 77L and the movable lens units 80R, 80L are chosen such that the light flux from the pupils of the eye on the optical paths from the objective lenses 77R, 77L to the movable lens units 80R, 80L and the optical paths from the movable lens units 80R, 80L to the visual targets 63R, 63L become parallel. Thus, the light flux emerging from the visual targets parallel to the optical axis are focused on the anterior eye parts of the eyes to be examined. Because of such a construction, even if alignment work such as eye width adjustment is done, no deviation of focus, magnification and measured pupil diameter will occur in the image picked up by the image pickup element 83. However, since the relation between the fundus of the eye and the apparatus varies, compensation related to the distance between the pupils is necessary. Also, even if the movable lens units 80R and 80L are moved, the sizes of images of the visual targets 64R and 64L will not vary.

In the fourth embodiment, two dichroic mirrors 78 and 79 are provided in the visual target systems 76R and 76L and the observation and measurement of the anterior eye parts are effected by the use of two switchover mirrors 81 and 84. But if design of this embodiment is made such that the observation system and the measuring system are divided behind the switchover mirrors, it will be possible to reduce the number of the switchover mirrors to one and thus, the construction of the embodiment will be simplified.

Figure 13A:
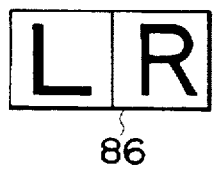
FIGS. 13A and 13B are illustrations of an illuminating switch.
Figure 13B:
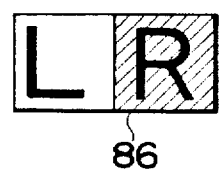

FIGS. 13A and 13B are illustrations of an illuminating switch 86 for the left and right visual target systems 76L and 76R. The left and right eye visual target systems 76L and 76R are designed to be capable of being discretely illuminated and turned off as required, and FIG. 13A shows a state in which both of the left and right eye visual target systems 76L and 76R are illuminated, and FIG. 13B shows a state in which the left eye visual target system 76L is illuminated and the right eye visual target system 76R is turned off. By utilizing the state in which the left and right visual target systems are illuminated or turned off, the measurement of heterophoria is possible. For example, in a state in which the left and right eye visual target systems 76L and 76R are illuminated at one time and presented to the examinee, the eye to be examined for effecting the measurement of heterophoria is observed by means of an anterior eye part observation infrared TV set, not shown. In this state, the illuminated measurement side visual target system is turned off and the movement of the eye to be examined is observed. If heterophoria is present, the eye will move and therefore, if the amount of movement of the visual axis is calculated by the use of a video signal, the degree of heterophoria will be found. Also, the heterophoria then the device is adjusted so that the eye is in a state of relaxed far sight can be examined by means of the both eye visual targets.

As described above, measurement is effected by the use of the two independent visual target systems and therefore, the elimination of instrument myopia is possible and accurate measurement can be accomplished. Also, measurement is effected while the left and right eye refraction measuring means are changed over and therefore, a single measuring optical system is only required, and this leads to a low cost for the device. Also, the switchover of the left and right eyes to be examined becomes possible without the examinee moving his or her face.

Figure 14:
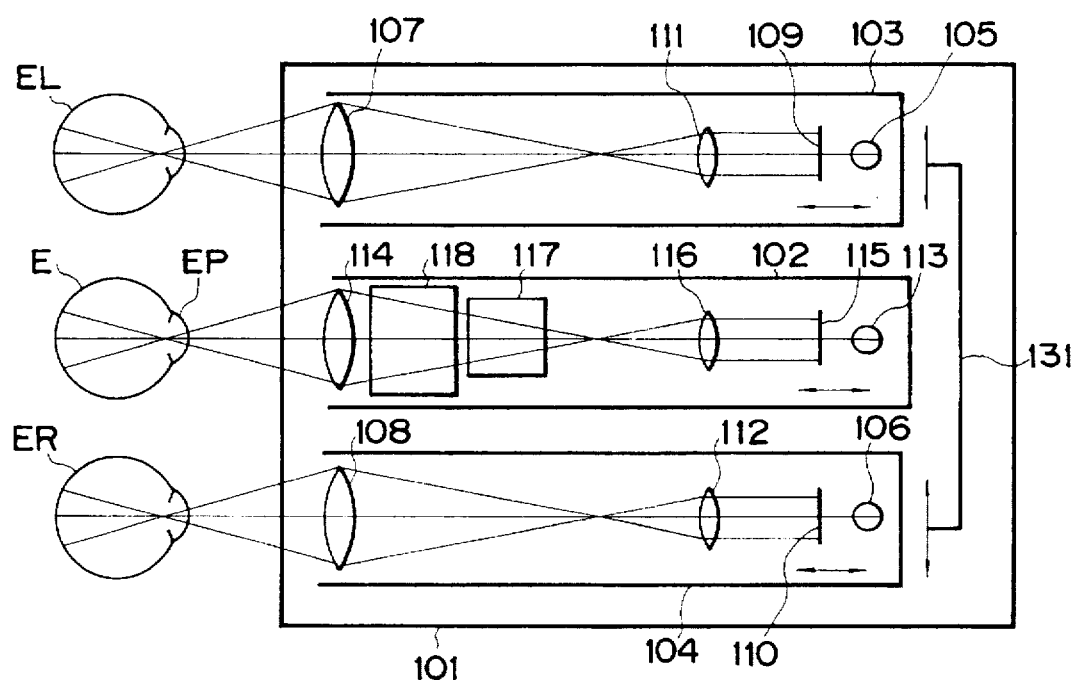
FIG. 14 shows the construction of an optical system as it is seen from above the body of an eye refractometer according to a fifth embodiment of the present invention.
Figure 15:
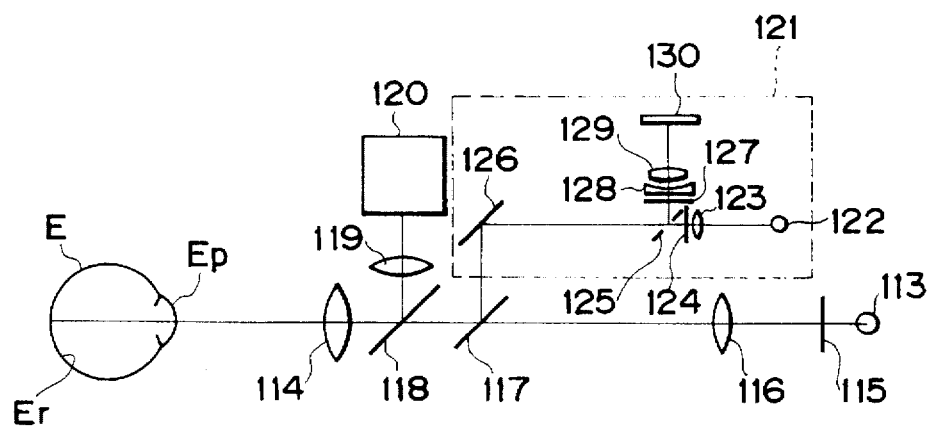
FIG. 15 shows the construction of the optical system as it is seen from side ways of a visual target projecting unit for an eye to be examined.

FIG. 14 shows the construction of the interior of an eye refractometer body 101 according to a fifth embodiment of the present invention as it is seen from above it, and FIG. 15 shows the construction of a visual target projecting unit for an eye to be examined as it is seen from the side thereof, and there are provided a visual target projecting unit 102 for the eye to be examined, and other eye visual target projecting units 103 and 104 for the left eye EL and right eye ER. On the optical paths from illuminating lamps 105, 104 for other eye visual target projecting units 103, 104 to objective lenses 107, 108, there are disposed visual targets 109, 110 driven along the optical paths and lenses 111, 112.

As shown in FIG. 15, on the optical path from an illuminating lamp 113 for the visual target projecting unit 102 for the eye to be examined to an objective lens 114, there are disposed a visual target 115 driven along the optical path, a lens 116 and dichroic mirrors 117, 118, and on the optical path in the direction of reflection of the dichroic mirror 118, there are disposed a lens 119 and a TV camera 120. Also, on the optical path in the direction of reflection of the dichroic mirror 117, there is disposed an objective eye refraction measuring unit 121, and on the optical path from a light source 122 for measurement in the objective eye refraction measuring unit 121 to the dichroic mirror 117, there are disposed a lens 123, a stop 124, an apertured mirror 125 and a mirror 126, and on the optical path in the direction of reflection of the apertured mirror 125, there are disposed a multiaperture stop 127, a separating prism 128, a lens 129 and an image pickup element 130.

Figure 16:
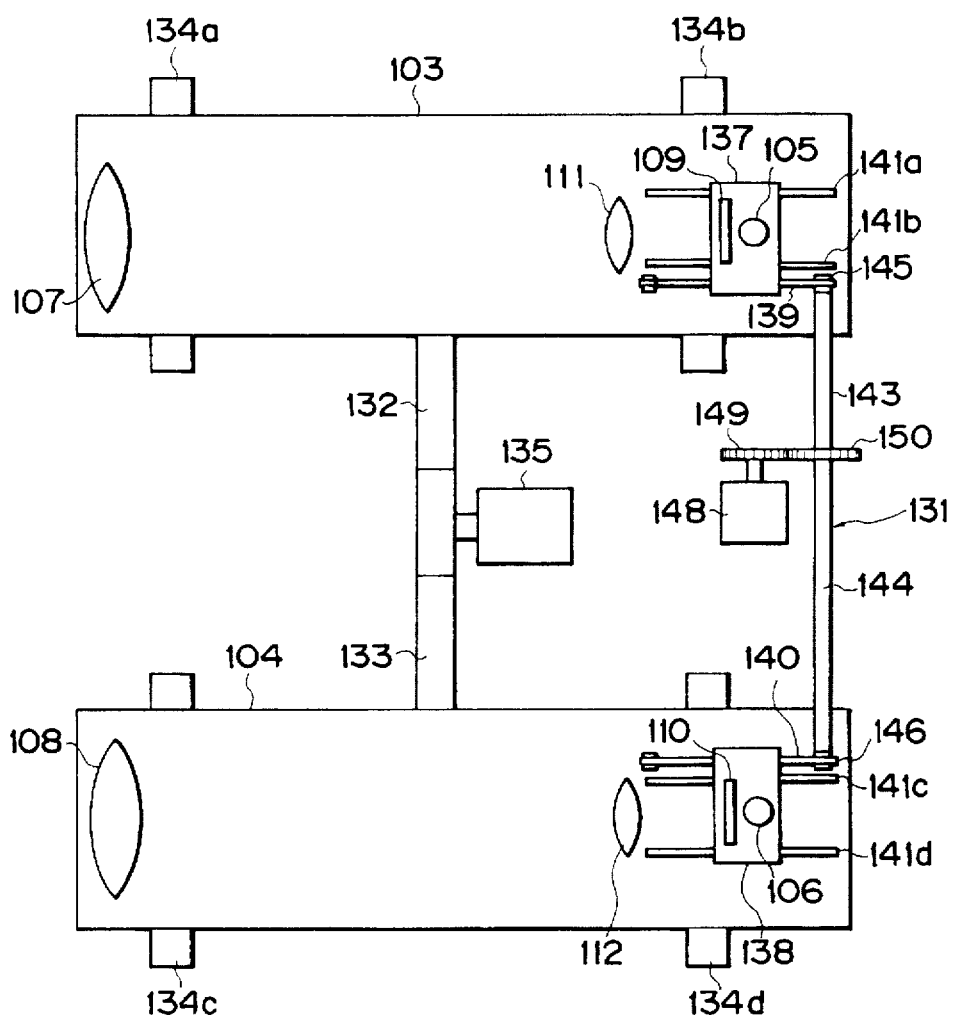
FIG. 16 shows the construction of the cooperating means of the visual target projecting unit.
Figure 17:
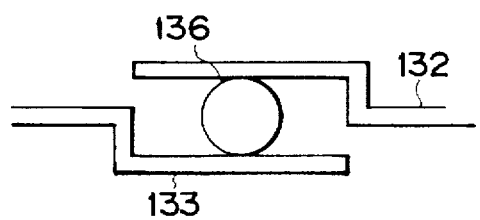
FIG. 17 illustrates the state of meshing engagement between a connecting member and a shaft.

Further, the visual target projecting units 103 and 104 for the other eye are designed to be moved to the left and to the right by cooperating means 131 of the visual target projecting unit. FIG. 16 shows the construction of this cooperating means 131 of the visual target projecting unit, and the visual target projecting units 103 and 104 for the other eye are connected to connecting members 132 and 133, respectively, and are placed on rails 134a–134d. As shown in FIG. 17, the connecting members 132 and 133 are in meshing engagement with a shaft 136 rotated by a drive motor 135. The illuminating lamp 105 and visual target 109 for the visual target projecting unit 103 for the other eye and the illuminating lamp 106 and visual target 110 for the visual target projecting unit 104 for the other eye are provided on members 137 and 138, respectively, and the members 137 and 138 each have one end thereof fixed to belts 139 and 140 and are provided for movement in the direction of the optical axis along guide rails 141a–141d. One end of each of the belts 139 and 140 is turned around pulleys 145 and 146 provided on two shafts 143 and 144 joined together.

Figure 18:
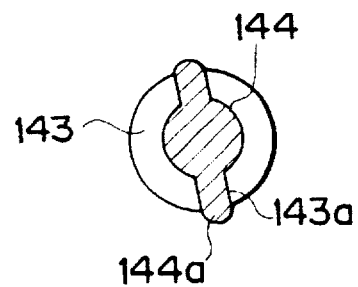
FIG. 18 illustrates the joined state of shafts.

As shown in FIG. 18, the joined portion of the shafts 143 and 144 is axially expansible and contractible with the projections 144a of the shaft 144 engaged with the cut-ins of the shaft 143. Further, a gear 150 in meshing engagement with a gear 149 provided on the shaft of a drive motor 148 is provided on the shafts 143, 144.

Figure 19:
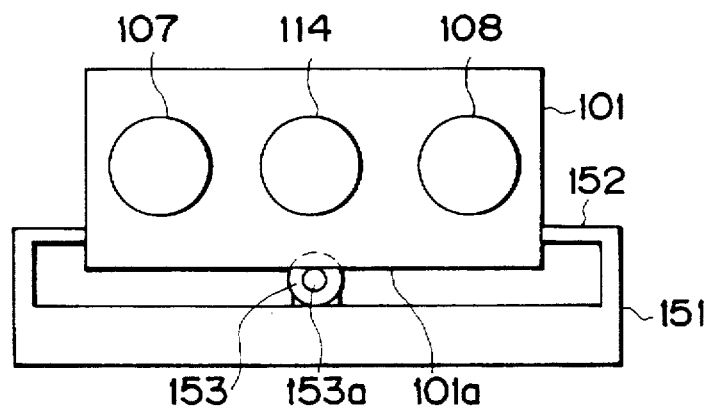
FIG. 19 shows the construction of a mechanism for measuring the distance between pupils.

The eye refractometer body 101 is provided on a fixed base 151, as shown in FIG. 19, and is slidable along a guide member 152. A potentiometer 153 is secured to the fixed base 151, and the shaft 153a thereof is rotatable while being in contact with the bottom surface 101a of the eye refractometer body 101.

Figure 20:
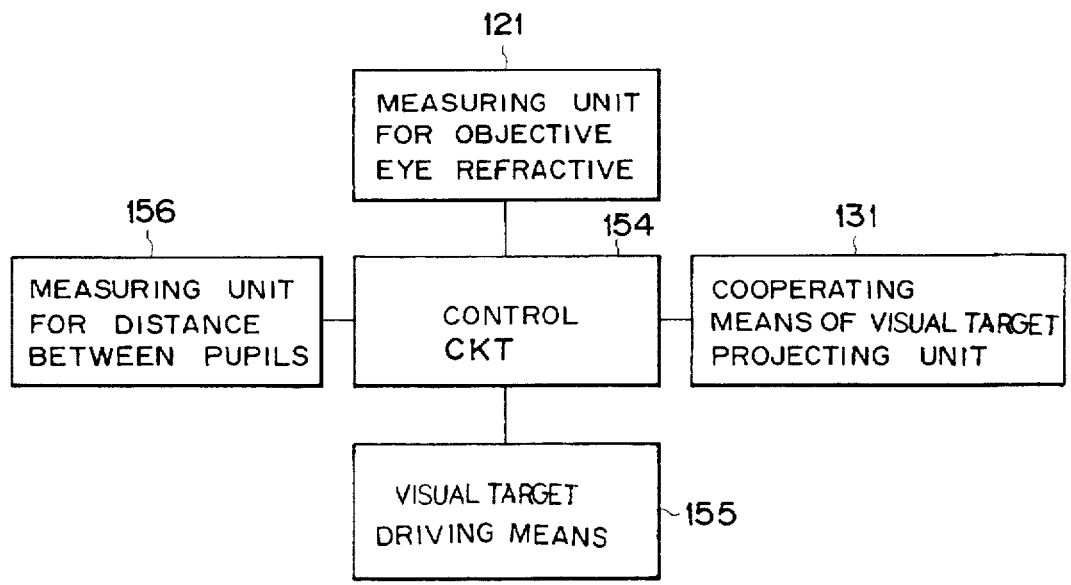
FIG. 20 is a block diagram of a control circuit.

Also, a control circuit is provided to control the cooperating means 131 of visual target projecting unit. FIG. 20 is a block diagram of the control circuit, and as shown, the control circuit 154 has connected thereto a measuring unit 121 for objective eye refraction, cooperating means 131 of the visual target projecting unit driven by a drive motor 137 shown in FIG. 16, visual target driving means 155 driven by a drive motor 148, and a measuring unit 156 for measuring the distance between the pupils comprising the potentiometer 153, etc. shown in FIG. 19.

During the measurement of eye refraction, the distance between the pupils is first measured. The optical axis of the visual target projecting unit 102 for the eye to be examined is adjusted to the visual axes of the right eye ER and left eye EL by sliding the eye refractometer body 101 to left and right along the guide member 152 shown in FIG. 19. At this time, the eye refractometer body 101 is slid to the left and to the right, whereby the shaft 153a of the potentiometer 153 is rotated and the amount of this rotation is converted into the amount of movement of the eye refractometer body 101 in the measuring unit 156 for measuring the distance between the pupils and then the distance between pupils is obtained.

The alignment of the visual target projecting unit 102 for the eye to be examined is effected while the anterior eye parts of the right eye ER and left eye EL are observed. The beam of light from the anterior eye part passes through the lens 114, the dichroic mirror 118 and the lens 119, is picked up as an anterior eye part image by the TV camera 120, and is displayed on a TV monitor, not shown. The examiner can effect the alignment while observing this TV monitor.

The result of the measurement in the measuring unit 156 for measuring the distance between the pupils by obtaining the output of the potentiometer 153 is outputted to the control circuit 154, and on the basis of this result, the cooperating means 131 of the visual target projecting unit is driven and the spacing between the visual target projecting units 103 and 104 for the other eye is adjusted in conformity with the eye width. When the drive motor 135 is started, the shaft 136 is rotated to thereby move the connecting members 132 and 133 in opposite directions, whereby the spacing between the visual target projecting units 103 and 104 for the other eye is widened or narrowed. With the movement of the visual target projecting units 103 and 104 for the other eye, the shafts 143 and 144 are expanded or contracted.

Also, the measuring unit 156 for measuring the distance between pupils detects whether the eye E to be examined is the right eye ER or the left eye EL, and when the eye refractometer body 101 is slid and the left eye EL is aligned with the visual target projecting unit 102 for the eye to be examined, the visual target projecting unit 104 for the other eye, moved in advance by the visual target projecting unit driving means 131, automatically coincides with the right eye ER. Also, in a case where the right eye ER is the object of measurement, when the visual target projecting unit 102 for the eye to be examined is aligned with the right eye ER, the visual target projecting unit for the other eye 103 automatically coincides with the left eye EL.

Figure 21:
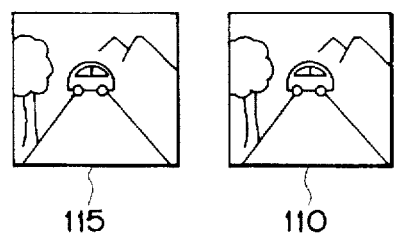
FIG. 21 is an illustration of a visual target for far fixation.

When the illuminating lamps 105, 106 and 113 are turned on, the beams of light from the illuminating lamps 105 and 106 illuminate the visual targets 109 and 110, respectively, and pass through the lenses 111 and 112, respectively, and are projected onto the fundus Ey of the eye E to be examined. The beam of light from the illuminating lamp 113 passes through the lens 116, the dichroic mirrors 117, 118 and the lens 114, and is projected onto the fundus Er of the eye to be examined. The visual targets 109, 115 or the visual targets 110, 115 are presented to the two eyes and the fixation of the two eyes is performed. The visual targets 109, 115 and the visual targets 110, 115, as shown in FIG. 21, are one set of stereoscopic photographs, which are transparent films. When these are view by the examinee, it is possible to have the examinee have the sense of actually seeing a distant scene and therefore, the accomodation of the eye can be eliminated.

A slide stereoscopic photograph of a close-range view can be used for near fixation of the gaze of the eye, and in contrast with the visual target 115 for the eye to be examined, the visual target 109 for the left eye EL and the visual target 110 for the right eye ER can be slide photographs taken with a camera deviated in opposite directions.

Also, computer graphics, instead of slide photographs, may be used as the visual targets 109, 110 and 115. For far fixation of the gaze of the eye, the photographs may be prepared so as to create the sense of seeing the farthest area in the central portion, and for near fixation of the gaze of the eye, the photographs may be prepared so as to create the sense of seeing the nearest area in the central portion.

Figure 22:
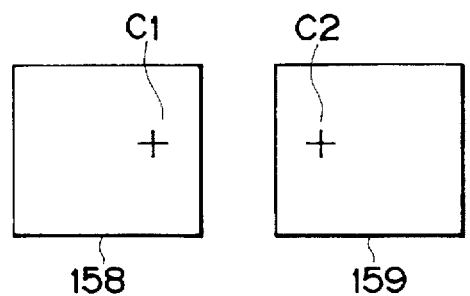
FIG. 22 is an illustration of a visual target for near fixation.
Figure 23:
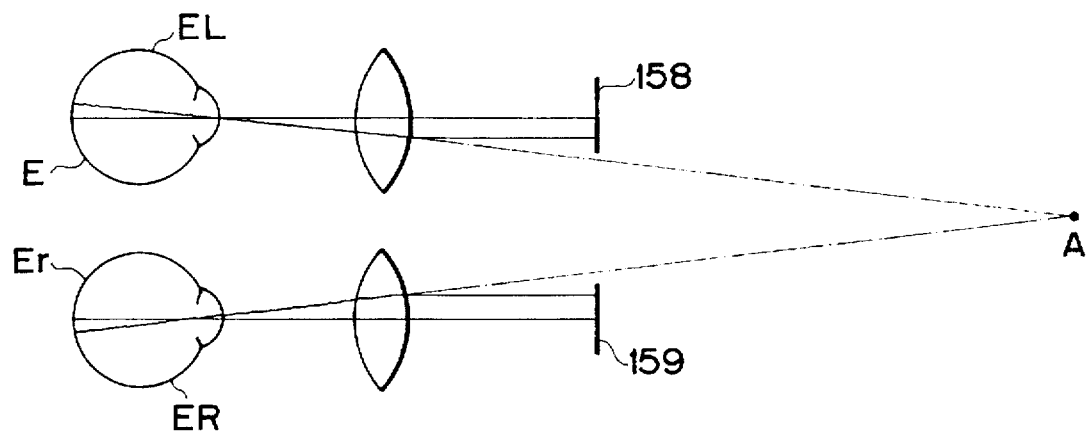
FIG. 23 illustrates the congestion of the visual target for near fixation.

FIG. 22 shows visual targets for near fixation of the gaze of the eye prepared by computer graphics, and as shown, the crosses C1 and C2 of a visual target 158 for the eye to be examined and a visual target 159 for the right eye ER when the left eye EL is the object of measurement are made eccentric relative to each other. When the fixation of the two eyes is effected by means of these visual targets 158 and 159, the visual axes of the eye E to be examined and the right eye ER become congested as shown in FIG. 23, and the examinee feels as if the crosses C1 and C2 of the visual targets 158 and 159 overlap each other at a point A. Therefore, also in the visual target projecting unit 162 for the eye to be examined and the visual target projecting unit 104 for the other eye which are disposed parallel to each other, the crosses C1 and C2 of the visual targets 158 and 159 are congested at the near point A and are image-fused by the two eyes and therefore, the diopter of the eye E to be examined can be guided to a near point. If only the cross C2 of the visual target 159 is made eccentric, the examinee will feel as if the crosses C1 and C2 of the visual targets 158 and 159 overlap each other at a point on the visual axis of the right eye ER and therefore, the refractive power at lutea (yellow spot) can be measured.

The apparent diopters of the visual targets 109 and 110 are adjusted by controlling the visual target driving means 155 by the control circuit 154. When the drive motor 148 is started, the gear 149 is rotated to thereby rotate the gear 150 and rotate the shafts 143 and 144. In operative association with the shafts 143 and 144, the pulley 145 and 146 are rotated to thereby rotate the belts 139 and 140, and with the members 137 and 138, the lamps 105, 106 and the visual targets 105 and 110 are moved by the same amount along the optical axes, and the diopters of the visual targets 109 and 110 for the right eye ER and the left eye EL are varied at one time. The apparent diopter of the visual target 115 is likewise varied to thereby enable the visual targets 109 and 115 or the visual targets 110 and 115 to be clearly seen by the two eyes.

When the light source 122 for measurement of the objective eye refraction measuring unit 121 is turned on after the fixation of the gaze of the eye of the examinee is complete the beam of light from the light source 122 for measurement passes through the lens 123, the stop 124, the apertured mirror 125, the mirror 126, the dichroic mirrors 117, 118 and the lens 114 and is projected on the fundus Ey of the eye. The reflected beam of light from the fundus Ey of the eye returns along the same optical path, is reflected by the apertured mirror 125, passes through the multiaperture stop 127, the separating prism 128 and the lens 129 and is received by the image pickup element 130. From the positions of received light, the refractive power of the eye E to be examined is calculated, and the result of the measurement is outputted from the control circuit 154.

On the basis of the result of this measurement, the visual target driving means 155 is controlled by the control circuit 154, and the apparent diopters of the visual targets 109 and 110 for the other eye are adjusted again. Even when the eye refractometer body 101 is slid for measuring the other eye, the measurement of refraction could be immediately started by the objective eye refraction measuring unit 121 because the visual targets are clearly presented to the two eyes.

Figure 24:
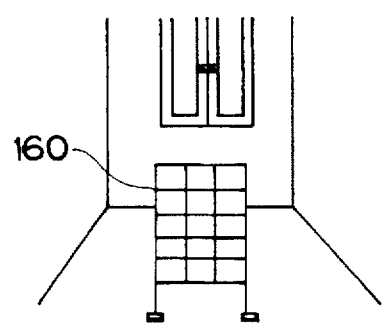
FIG. 24 illustrates the arrangement of a visual target for optometry.

As regards the visual targets 109, 110 and 115, the visual target for far fixation of the gaze of the eye or the visual target for near fixation of the gaze of the eye may be used in accordance with the purpose of measurement. Also, as shown in FIG. 24, a visual target 160 for optometry may be disposed in the room so that subjective eye refraction measurement may be effected simultaneously with objective eye refraction measurement.

Figure 25A:
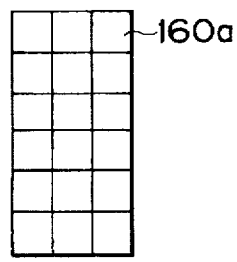
FIGS. 25A, 25B and 25C are front views of the visual target for optometry.
Figure 25B:
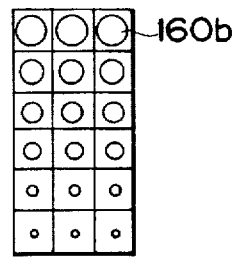
Figure 25C:
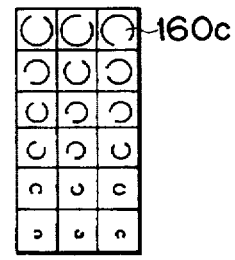

The visual target 160 for optometry, as shown in FIGS. 25A, 25B and 25C comprises a visual target 160a for the other eye comprising frames alone, a visual target 160b for the other eye comprising continuous circles of Landolt rings, and a visual target 160c for the eye to be examined using a Landolt ring figure. The visual targets 160a and 160b are presented from one of the visual target projecting units 103 and 104 for the other eye, and the visual target 160c is presented from the visual target projecting unit 102 for the eye to be examined, and the examinee is told to see the entire visual target 160 for optometry with the two eyes. The visual target 160b is for fusion, and only the eye E to be examined sees the visual target 160c. The value of the eye refraction is measured from the response of the examinee to the Landolt ring figure of the visual target 160c. A cross cylinder can be inserted into the visual target projecting unit 102 for the eye to be examined to thereby correct astigmatism.

Figure 26:
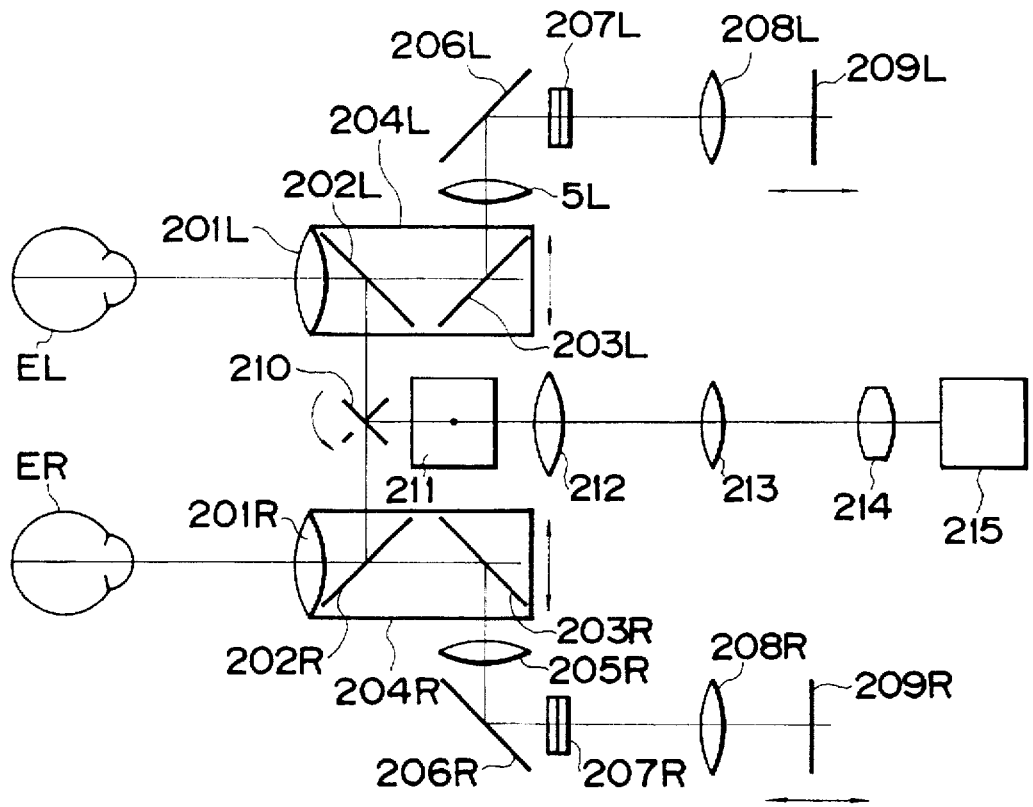
FIG. 26 shows the construction of a sixth embodiment of the present invention as it is seen from above it.
Figure 27:
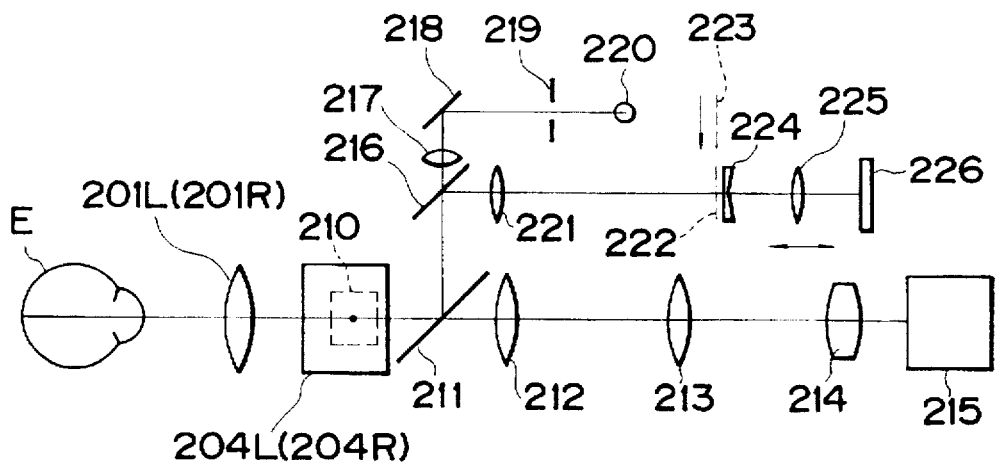
FIG. 27 shows the construction of the sixth embodiment as it is seen from sideways thereof.

FIG. 26 shows the construction of a sixth embodiment as it is seen from above it, and FIG. 27 shows the construction of the optical system as it is seen from the side thereof. Dichroic mirrors 202L, 202R and mirrors 203L, 203R are disposed in succession behind objective lenses 201L, 201R, respectively, opposed to the left eye EL and the right eye ER, whereby mirror unit 204L, 204R are constituted and are movable in the direction of the eye width as indicated by arrow. On the respective optical paths in the direction of incidence of the mirrors 203L and 203R, there are disposed lenses 205L, 205R, mirrors 206L, 206R, cross cylinders 207L, 207R comprising the same two cylindrical lenses, lenses 208L, 208R and visual targets 209L, 209R movable along the optical paths as indicated by arrows.

A switchover mirror 210 rotatable in the plane of the drawing sheet is disposed between the dichroic mirrors 202L and 202R, and a dichroic mirror 211, a lens 212, a field lens 213, a lens 214 and a TV camera 215 are disposed on the optical path in the direction of reflection of the switchover mirror 210, and a TV monitor, not shown, is connected to the TV camera 215. The field lens 213 and lens 214 may be omitted depending on the design.

As shown in FIG. 27, an objective refractive power measuring unit is constructed on an optical path extending above the dichroic mirror 211. A half mirror 216, a lens 217, a mirror 218, a small-aperture stop 219 and a measuring light source 220 are disposed on the optical path above the dichroic mirror 211, and on the optical path in the direction of reflection of the half mirror 216, there are disposed a lens 221, ring stops 222, 223 selectively inserted into the optical path, a separating prism 224 comprising six wedge prisms or six inverted conical Axicons, a lens 225 movable along the optical path as indicated by the arrow, and a photoelectric sensor 226 such as a CCD image pickup element. The half mirror 216 may be replaced by an apertured mirror.

The dichroic mirrors 202L, 202R and dichroic mirror 211 have the spectral characteristic of transmitting visible light therethrough and reflecting infrared light. The cross cylinders 207L and 207R are disposed at the focal positions of the lenses 205L and 205R, respectively, through the mirrors 206L and 206R, the measuring light source 220 has a conjugate relation with the fundus of an ammetropic eye, and the small-aperture stop 219 and ring stops 222, 223 have a conjugate relation with the pupil Ep of the eye E to be examined. Also, the small-aperture stop 219 has the center of its opening on the optical axis, and the ring stops 222 and 223 have openings of different sizes, and light intercepting portions are provided at the centers of these openings to thereby form annular openings.

The beams of reflected light from the anterior eye parts of the left eye EL and right eye ER by the anterior eye illuminating light pass through the objective lenses 201L and 201R, respectively, and are reflected by the dichroic mirrors 202L and 202R, respectively, and the switchover mirror 210 reflects one of the beams of light to the right. This beam of reflected light passes through the dichroic mirror 211 and the lens 212, is once imaged by the field lens 213, passes through the lens 214, is photographed as an anterior eye part image Pf by the TV camera 215 and is displayed on the TV monitor.

The examiner sights the anterior eye part image so that the pupil Ep may be positioned on the front focal planes of the objective lenses 201L and 201R while observing the TV monitor, and moves the apparatus so that the beam of measuring light may not be eclipsed from the pupil Ep.

The switchover of the eye to be examined which should be observed is effected by the switchover mirror 210, when alignment is to be performed with respect to the left eye EL, the reflecting surface of the switchover mirror 210 is opposed to the dichroic mirror 202L as indicated by solid line, and the beam of light from the anterior eye part of the left eye EL is directed to the TV camera 215. When conversely, alignment is to be performed with respect to the light eye ER, the reflecting surface of the switchover mirror 210 can be opposed to the dichroic mirror 202R as indicated by dot-and-dash line.

When the diopter guide of the examinee is to be effected, the visual targets 209L and 209R are presented to the left eye EL and right eye ER, respectively. The beams of light from the visual targets 209L and 209R pass through the lenses 208L, 208R and the cross cylinders 207L, 207R, are reflected by the mirrors 206L, 206R, pass through the lenses 205L, 205R, are reflected by the mirrors 203L, 203R, pass through the dichroic mirrors 202L, 202R and the objective lenses 201L, 201R, and are projected onto the funduses of the left eye EL and right eye ER, and the visual targets 209L and 209R are seen by the two eyes. The two cylindrical lenses of the cross cylinders 207L and 207R are rotated in opposite directions and the astigmatism of the left eye EL and right eye ER is corrected. Also, the visual targets 209L and 209R are moved along the optical axis to thereby adjust the diopter so that the examinee can clearly see the visual targets 209L and 209R. The visual targets 209L and 209R are then gradually moved to guide the examinee's diopter.

After the above-described diopter guide, the measuring light source 220 is turned on and the refractive power is measured. The beam of light from the measuring light source 220 passes through the small-aperture stop 219, the mirror 218 and the lens 217, is reflected by the dichroic mirror 211, is reflected to one of the left and right directions by the switchover mirror 210, is reflected by the dichroic mirror 202L or 202R, passes through the objective lens 201L or 201R and is projected onto the fundus of the left eye EL or the right eye ER. The beam of reflected light here returns along the same optical path, is reflected by the switchover mirror 210 and the dichroic mirror 211, passes through the ring stop 222 or 223, the separating prism 224 and the lens 225, and is received as a ring light beam image by the photoelectric sensor 226.

The lens 225 is adjusted to the diopters of the visual targets 209L, 209R and is moved along the optical axis, and the focus of the ring light beam image is adjusted, and the eye refractive power is obtained on the basis of the light reception signal of the photoelectric sensor 226. The selection of the eye to be examined is effected by the switchover mirror 210 as during the observation, and to measure the left eye EL, the switchover mirror 210 is rotated to the position of solid line, and to measure the light eye ER, the switchover mirror 210 is rotated to the position of dot-and-dash line. One of the ring stops 222 and 223 is inserted into the optical path in accordance with the diameter of the pupil Ep of the eye E to be examined. Instead of the ring stops 222 and 223, use can be made of a six-aperture stop having six openings symmetrical with respect to the optical axis.

In this case, the beam of measuring light is received as spot light beam images comprising six small circles by the photoelectric sensor.

In this embodiment, when the mirror units 204L and 204R are moved in the direction of the eye width and the distances between the dichroic mirrors 202L, 202R and the lens 221 are varied, the beams of light from the left eye EL and the right eye ER are made parallel in the optical path after passing the objective lenses 201L and 201R and therefore, the conjugate relations of the small-aperture stop 219 and the ring stop 222 or 223 with the pupil Ep of the eye E to be examined are preserved, but the position of the beam of light on the photoelectric sensor 226 varies according to the change of distance between the mirror units 204L and 204R.

Therefore, when calculating the refractive power, the distance between the mirror units 204L and 204R or the amount of movement of the lens 225 should be taken into account. The lens 225 may be fixed, but if it is made movable, a sharp ring light beam image can be received by the photoelectric sensor 226, and this leads to the improved accuracy of the measured value.

If as the visual targets 209L and 209R, an eyesight test chart comprising a Landolt ring or the like is presented to the examinee and the examinee is instructed to visually respond thereto, subjective eye refractive power measurement will also be possible.

Figure 28:
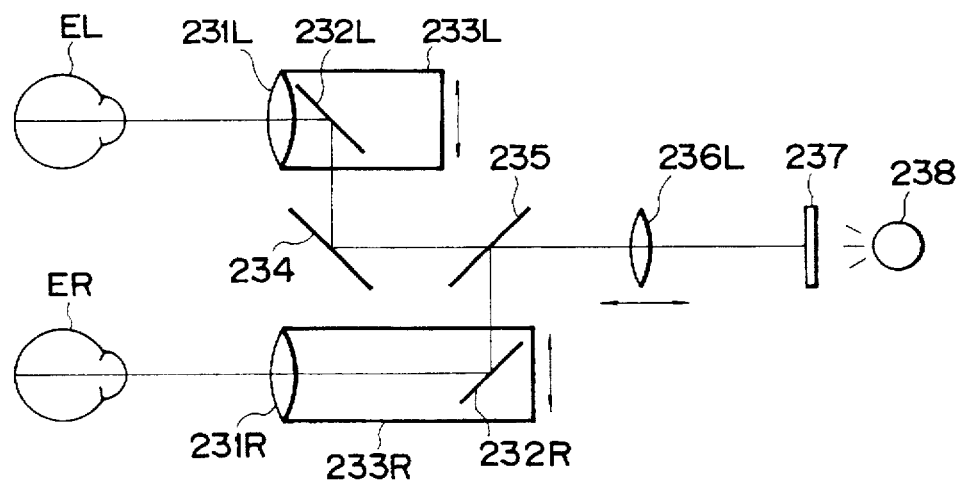
FIG. 28 shows the construction of a seventh embodiment of the present invention as it is seen from above it.

FIG. 28 shows the construction of a seventh embodiment of the present invention, and as shown, mirrors 232L and 232R are disposed behind objective lenses 231L and 231R, respectively, opposed to the left eye EL and the right eye ER, to thereby constitute mirror units 233L and 233R movable in the direction of the eye width. A mirror 234 and a half mirror 235 are disposed on the optical paths, respectively, in the direction of reflection of the mirrors 232L and 232R, and a half mirror 235, a lens 236 movable along the optical axis, a visual target 237 and a light source 238 are disposed in succession behind the mirror 234.

The beam of light from the light source 238 illuminates the visual target 237 from behind it and passes through the lens 236, and is divided into two directions by the half mirror 235. The beam of light transmitted through the half mirror 235 is reflected by the mirror 234 and mirror 232L, passes through the objective lens 231L and is projected onto the fundus of the left eye EL. On the other hand, the beam of light reflected by the half mirror 235 is reflected by the mirror 232R, passes through the objective lens 231R and is projected onto the fundus of the right eye ER. The examiner moves the mirror units 233L and 233R in the direction of the eye width and effects alignment so that the visual target 237 may be presented to the two eyes EL and ER, and subsequently moves the lens 236 along the optical axis so that the examinee can see the visual target 237.

When for example, subjective eye refractive power measurement is to be done in the actual examination, an examinee can be let to recognize the target 237 and to respond. Also, when objective eye refractive power measurement is to be effected, the lens 236 is moved to the far point side or the near point side to the limit at which the examinee becomes unable to see visual target 237 clearly, whereby the diopter is guided. The diopter of the visual target 237 during subjective eye refractive power measurement may be set on the basis of the result of objective eye refractive power measurement.

In this embodiment, the beams of light from the pupils Ep of the left eye EL and right eye ER are not made parallel to the optical path by the objective lenses 231L and 231R and therefore, the conjugate surface with the pupils Ep varies in conformity with a variation in the spacing between the mirror units 233L and 233R and further, the relation between the diopter of the visual target 237 and the position of the lens 236 varies. Accordingly, it is necessary to determine the amounts of movement of the lens 236, the optics coupled with this visual target system (not shown) of the objective eye refractive power measuring unit, etc. in accordance with the spacing between the mirror units 233L and 233R.

What is claimed is:

1. An eye refractometer comprising:

at least two visual target systems, wherein each of said at least two visual target systems has a visual target and diopter varying means for making said visual target variable in diopter;

eye refractive power measuring means for projecting light to an eye to be examined and receiving the reflected light to measure the refractive power of the eye;

optical path coupling means for coupling at least one of the optical paths of said visual targets and an optical path of said eye refractive power measuring means at a position between the eye and said diopter varying means; and switchover means for switching over at least part of said eye refractive power measuring means from one to another between both eyes of an examinee.

2. An eye refractometer according to claim 1, wherein the number of said visual target systems is two, said optical path coupling means is provided for each of said two visual target systems, and said switchover means has a switchover mirror for turning the optical path of said eye refractive power measuring means alternately to said two optical path coupling means.

3. An eye refractometer according to claim 1, wherein the number of said visual target systems is two, said optical path coupling means is provided for each of said two visual target systems, and said switchover means has a moving mechanism for moving the optical path of said eye refractive power measuring means to a position in which it can be coupled to each of said two optical path coupling means.

4. An eye refractometer according to claim 1, further having an anterior eye part observation system for effecting anterior eye part observation, and means for switching over the eye to be examined be observed by means of said anterior eye part observation system to the right and to the left.

5. An eye refractometer according to claim 1, further having cornea shape measuring means for measuring the shape of the cornea of the eye to be examined.

6. An eye refractometer according to claim 1, further having means for measuring the refraction information of a pair of spectacles.

7. An eye refractometer according to claim 1, further having width adjusting means for adjusting the width of said visual target systems in accordance with the eye width of the eye to be examined.

8. An eye refractometer according to claim 1, wherein said visual target systems can be arranged in a direction inclined with respect to a horizontal direction.

9. An eye refractometer according to claim 1, further having a switch for turning off the visual target of one of said visual target systems.

10. An eye refractometer comprising:

at least two visual target systems each having visual targets and diopter varying means for making said visual targets variable in diopter;

eye refractive power measuring means for projecting light to an eye to be examined and receiving the reflected light to measure the refractive power of the eye;

optical path coupling means for coupling at least one of the optical paths of said visual targets and an optical path of said eye refractive power measuring means at a position between the eye and said diopter varying means; and conjunction means for making the diopters of said diopter varying means of said at least two visual target systems vary in conjunction with each other.

11. An eye refractometer comprising:

at least two visual target systems, each having visual targets and diopter varying means for moving a lens to make said visual targets variable in diopter;

eye refractive power measuring means for projecting light to an eye to be examined and receiving the reflected light to measure the refractive power of the eye; and optical path coupling means for coupling at least one of the optical paths of said visual targets and an optical path of said eye refractive power measuring means at a position between the eye and said diopter varying means;

wherein in each of said visual target systems, an optical member is disposed so that a beam of light leaving the visual target parallel to the optical axis is focused on the anterior segment of the eye to be examined.

12. An eye refractometer comprising:

at least two visual target systems having visual targets and diopter varying means for making said visual targets variable in diopter;

eye refractive power measuring means for projecting light to an eye to be examined of an examinee and receiving the reflected light to measure the refractive power of the eye;

optical path coupling means for coupling at least one of the optical paths of said visual targets and an optical path of said eye refractive power measuring means at a position between the eye and said diopter varying means;

sliding means for moving at least part of said visual target systems in the direction of the distance between the pupils of the eyes of the examinee;

movement amount measuring means for measuring the distance between the pupils of the examinee using the amount of movement performed by said sliding means; and spacing adjusting means for adjusting the spacing between said visual target systems on the basis of the result of the measurement by said movement amount measuring means.

13. An eye refractometer comprising:

at least two visual target systems having visual targets and diopter varying means for making said visual targets variable in diopter;

eye refractive power measuring means for projecting light to an eye to be examined and receiving the reflected light to measure the refractive power of the eye;

optical path coupling means for coupling at least one of the optical paths of said visual targets and an optical path of said eye refractive power measuring means at a position between the eye and said diopter varying means; and inclination adjusting means for inclination-adjusting said visual target systems and said eye refractive power measuring means as a unit.

14. An eye refractometer comprising:

at least two visual target systems each having visual targets and diopter varying means for making said visual targets variable in diopter, said diopter varying means of said at least two visual target systems varying diopters thereof; and eye refractive power measuring means for projecting light to an eye to be examined and receiving the reflected light to measure the refractive power of the eye, said eye refractive power measuring means being arranged so that an optical path of said eye refractive power measuring means and at least one of the optical paths of said visual target systems have a common optical path.

* * * * *

UNITED STATES PATENT AND TRADEMARK OFFICE
CERTIFICATE OF CORRECTION

PATENT NO. : 5,777,718

DATED : July 7, 1998

INVENTOR : YOSHIMI KOHAYAKAWA

It is certified that error appears in the above-identified patent and that said Letters Patent is hereby corrected as shown below:

COLUMN 1:

Line 40, "invention." should read --embodiment.
Line 64, "side ways" should read --sideways--.

COLUMN 6:

Line 37, "bead" should read --head--.

COLUMN 11:

Line 25, "view" should read --viewed--.

COLUMN 13:

Line 62, "when" should read --When--.

UNITED STATES PATENT AND TRADEMARK OFFICE
CERTIFICATE OF CORRECTION

PATENT NO. : 5,777,718

DATED : July 7, 1998

INVENTOR : YOSHIMI KOHAYAKAWA

It is certified that error appears in the above-identified patent and that said Letters Patent is hereby corrected as shown below:

COLUMN 16:

Line 29, "be observed" should read --observed--.

COLUMN 17:

Line 8, "means;" should read --means,--.

Signed and Sealed this

Fifth Day of October, 1999

Attest:

Q. TODD DICKINSON

*Attesting Officer*   *Acting Commissioner of Patents and Trademarks*